United States Patent
Ternes et al.

(10) Patent No.: US 8,588,910 B2
(45) Date of Patent: Nov. 19, 2013

(54) NON-LINEAR DYNAMIC AV DELAY

(75) Inventors: David J. Ternes, Roseville, MN (US); Donald L. Hopper, Maple Grove, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 134 days.

(21) Appl. No.: 13/154,661

(22) Filed: Jun. 7, 2011

(65) Prior Publication Data

US 2012/0004697 A1  Jan. 5, 2012

Related U.S. Application Data (60) Provisional application No. 61/361,012, filed on Jul. 2, 2010.

(51) Int. Cl.
*A61N 1/00* (2006.01)

(52) U.S. Cl.
USPC ............................... 607/25; 607/9

(58) Field of Classification Search
USPC ........................................... 607/9, 25
See application file for complete search history.

(56) References Cited

U.S. PATENT DOCUMENTS

| | | | |
|---|---|---|---|
| 6,144,880 A | 11/2000 | Ding et al. | |
| 6,351,673 B1 | 2/2002 | Ding et al. | |
| 6,360,127 B1 | 3/2002 | Ding et al. | |
| 6,542,775 B2 | 4/2003 | Ding et al. | |
| 6,597,951 B2 | 7/2003 | Kramer et al. | |
| 6,622,040 B2 | 9/2003 | Ding et al. | |
| 6,684,103 B2 | 1/2004 | Ding et al. | |
| 6,856,836 B2 | 2/2005 | Ding et al. | |
| 6,859,665 B2 | 2/2005 | Ding et al. | |
| 6,915,160 B2 | 7/2005 | Auricchio et al. | |
| 6,961,616 B2 | 11/2005 | Kramer et al. | |
| 6,999,815 B2 | 2/2006 | Ding et al. | |
| 7,013,176 B2 | 3/2006 | Ding et al. | |
| 7,110,817 B2 | 9/2006 | Yu et al. | |
| 7,123,960 B2 | 10/2006 | Ding et al. | |
| 7,158,830 B2 | 1/2007 | Yu et al. | |
| 7,184,835 B2 | 2/2007 | Kramer et al. | |
| 7,203,540 B2 | 4/2007 | Ding et al. | |
| 7,231,248 B2 | 6/2007 | Kramer et al. | |
| 7,310,554 B2 | 12/2007 | Kramer et al. | |
| 7,460,908 B2 | 12/2008 | Krig et al. | |
| 7,616,993 B2 | 11/2009 | Mussig et al. | |
| 7,636,598 B2 | 12/2009 | Husby | |
| 7,653,436 B2 | 1/2010 | Schecter | |
| 7,904,156 B2 | 3/2011 | Maskara | |
| 7,904,157 B2 | 3/2011 | Casavant | |
| 2007/0191891 A1 | 8/2007 | Burnes et al. | |
| 2007/0191892 A1 | 8/2007 | Mullen et al. | |
| 2010/0016914 A1 | 1/2010 | Mullen et al. | |

OTHER PUBLICATIONS

Abraham, W T, "Cardiac Resynchronization in Chronic Heart Failure", New England Journal of Medicine, 346(24), (Jul. 13, 2002), 1845-1853.

(Continued)

*Primary Examiner* — Niketa Patel
*Assistant Examiner* — Mallika D Fairchild
(74) *Attorney, Agent, or Firm* — Schwegman Lundberg & Woessner, P.A.

(57) ABSTRACT

A non-linear dynamic specified AV delay can be used, such as to help maintain cardiac resynchronization therapy, such as in patients with one or more symptoms of congestive heart failure.

20 Claims, 4 Drawing Sheets

(56) References Cited

OTHER PUBLICATIONS

Auricchio, A., "Effect of Pacing Chamber and Atrioventricular Delay on Acute Systolic Function of Paced Patients With Congestive Heart Failure", Circulation, 99(23), (Jun. 15, 1999), 2993-3001.

Auricchio, A., et al., "Long-term clinical effect of hemodynamically optimized cardiac resynchronization therapy in patients with heart failure and ventricular conduction delay", J Am Coll Cardiol., 39, (Jun. 19, 2002), 2026-33.

Boriani, G., et al., "Randomized comparison of simultaneous biventricular stimulation versus optimized interventricular delay in cardiac resynchronization therapy", Am Heart J., 151(5), (May 2006), 1050-8.

Bristow, M. R, et al., "Cardiac-resynchronization therapy with or without an implantable defibrillator in advanced chronic heart failure", N Engl J Med., 350, (May 20, 2004), 2140-50.

De Lurgio, D. B., et al., "A comparison of cardiac resynchronization by sequential biventricular pacing and left ventricular pacing to simultaneous biventricular pacing: rationale and design of the DECREASE-HF clinical trial", J Card Fail., 11, (Apr. 2005), 233-239.

Gold, M. R, et al., "A prospective comparison of AV delay programming methods for hemodynamic optimization during cardiac resynchronization therapy", J Cardiovasc Electrophysiol., 18(5), (May 2007), 490-6.

Hunt, S. A, "ACC/AHA 2005 guideline update for the diagnosis and management of chronic heart failure in the adult", J Am Coll Cardiol., 46(6), (Sep. 20, 2005), e1-82.

Kass, D. A, "Cardiac resynchronization therapy", J Cardiovasc Electrophysiol., 16(Suppl 1), (Sep. 2005), S35-41.

Kass, D. A., "Improved Left Ventricular Mechanics From Acute VDD Pacing in Patients With Dilated Cardiomyopathy and Ventricular Conduction Delay", Circulation, 99(12), (Mar. 30, 1999), 1567-1573.

Linde, C., et al., "Long-term benefits of biventricular pacing in congestive heart failure: results from the MUltisite STimulation in cardiomyopathy (MUSTIC) study", J Am Coll Cardiol., 40, (Jul. 3, 2002), 111-8.

Perego, G. B, et al., "Simultaneous vs. sequential biventricular pacing in dilated cardiomyopathy: an acute hemodynamic study", Eur J Heart Fail., 5(3), (Jun. 2003), 305-13.

Rao, R. K, et al., "Reduced ventricular volumes and improved systolic function with cardiac resynchronization therapy: a randomized trial comparing simultaneous biventricular pacing, sequential biventricular pacing, and left ventricular pacing", Circulation, 115(16), (Apr. 24, 2007), 2136-2144.

Saxon, L. A, et al., "Effects of long-term biventricular stimulation for resynchronization on echocardiographic measures of remodeling", Circulation, 105(11), (Mar. 19, 2002), 1304-10.

Sharma, A. D, et al., "Percent Right Ventricular Pacing Predicts Outcomes in the DAVID Trial", Heart Rhythm, 2(8), (2005), 830-834.

Sogaard, P., et al., "Sequential versus simultaneous biventricular resynchronization for severe heart failure: evaluation by tissue Doppler imaging", Circulation, 106(16), (Oct. 15, 2002), 2078-84.

Stellbrink, Christoph, "Impact of Cardiac Resynchronization Therapy Using Hemodynamically Optimized Pacing on Left Ventricular Remodeling in Patients With Congestive Heart Failure and Ventricular Conduction Disturbances", Journal of the American College of Cardiology, vol. 38, No. 7, (Dec. 2001), 1957-1965.

Van Gelder, B. M., et al., "Effect of optimizing the VV interval on left ventricular contractility in cardiac resynchronization therapy", Am J Cardiol., 93(12), (Jun. 15, 2004), 1500-3.

Vanderheyden, M., et al., "Tailored echocardiographic interventricular delay programming further optimizes left ventricular performance after cardiac resynchronization therapy", Heart Rhythm, 2(10), (Oct. 2005), 1066-72.

Whinnett, Z. I, et al., "Haemodynamic effects of changes in atrioventricular and interventricular delay in cardiac resynchronisation therapy show a consistent pattern: analysis of shape, magnitude and relative importance of atrioventricular and interventricular delay", Heart, 92(11), (Nov. 2006), 1628-34.

Yu, C. M, et al., "Tissue Doppler Echocardiographic Evidence of Reverse Remodeling and Improved Synchronicity by Simultaneously Delaying Regional Contraction After Biventricular Pacing Therapy in Heart Failure", Circulation, 105(4), (Jan. 29, 2002), 438-445.

Yu, Yinghong, et al., "Biventricular mechanical asynchrony predicts hemodynamic effects of uni- and biventricular pacing", Am J Physiol Heart Circ Physiol, vol. 285, (2003), H2788-H2796.

NON-LINEAR DYNAMIC AV DELAY

CROSS-REFERENCE TO RELATED APPLICATIONS

This application claims the benefit of U.S. Provisional Application No. 61/361,012, filed on Jul. 2, 2010, under 35 U.S.C. §119(e), which is incorporated herein by reference in its entirety.

BACKGROUND

Cardiac rhythm management (CRM) devices can include implantable or other ambulatory devices, such as for monitoring or treating one or more cardiovascular conditions, such as pacemakers, cardioverter defibrillators, or devices that can provide a combination of pacing, defibrillation, cardiac resynchronization therapy (CRT), or the like. These devices can be used to detect and treat heart failure. In patients for whom CRT has been indicated for the treatment of heart failure, 100% biventricular pacing can be desirable in order to maintain cardiac synchrony and improve hemodynamic function of the heart. For example, Kramer et al. U.S. Pat. No. 6,961,616, entitled TRENDING OF CONDUCTION TIME FOR OPTIMIZATION OF CARDIAC RESYNCHRONIZATION THERAPY IN CARDIAC RHYTHM MANAGEMENT SYSTEM, mentions a device and method for optimizing cardiac resynchronization therapy delay over a patient's full range of activity by collecting data and generating an updatable template. (See Kramer et al. at Abstract; Col. 2, line 31-Col. 3, line 33.)

OVERVIEW

This document describes, among other things, an apparatus and method in which a non-linear dynamic AV delay interval (e.g., nonlinear with respect to the heart rate interval between successive contractions of the same heart chamber) can be used to maintain cardiac resynchronization therapy in patients with heart failure.

Example 1 can include subject matter that can include an apparatus comprising: a cardiac rhythm management device comprising: an atrial sensing circuit, configured to sense an atrial event; a ventricular pacing circuit configured to deliver biventricular pacing pulses; a ventricular sensing circuit configured to detect an intrinsic ventricular heart beat; a memory comprising instructions; and a processor, coupled to the atrial sensing circuit, the ventricular pacing circuit, the ventricular sensing circuit, and the memory, wherein the instructions, when executed by the processor, cause the processor to: schedule delivery to a heart of a biventricular pacing pulse to be delivered in response to expiration of a specified atrioventricular (AV) delay; upon detecting an intrinsic ventricular heart beat during the specified AV delay, shorten the specified AV delay used to deliver subsequent biventricular pacing pulses to promote biventricular pacing over an underlying intrinsic ventricular heart rhythm; and shorten the specified AV delay used to deliver subsequent biventricular pacing pulses by adjusting, or adjusting to, a non-linear mapping between AV delay and ventricular heart rate interval for scheduling delivery of a biventricular pacing pulse on a next cardiac cycle following the detected intrinsic ventricular heart beat during the specified AV delay.

In Example 2, the subject matter of Example 1 can optionally include the non-linear mapping including a piecewise linear mapping between AV delay and ventricular heart rate interval, wherein the processor circuit is configured to shorten the specified AV delay by adjusting the piecewise linear mapping.

In Example 3, the subject matter of any one of Examples 1-2 can optionally include the processor circuit configured to: measure a time difference between the intrinsic ventricular heart beat detected during the specified AV delay and the scheduled delivery of a biventricular pacing pulse; and subtract from the specified AV delay an amount based on the time difference to obtain a shortened specified AV delay.

In Example 4, the subject matter of any one of Examples 1-3 can optionally include the processor circuit configured to: measure a time difference between an atrial event and the intrinsic ventricular heart beat detected during the specified AV delay, wherein the atrial event and the intrinsic ventricular heart beat occur in the same cardiac cycle; divide the time difference by the specified AV delay to obtain a quotient value; and multiply the specified AV delay by the quotient value to obtain a shortened specified AV delay.

In Example 5, the subject matter of any one of Examples 1-4 can optionally include the processor circuit configured to, after a specified period of time following the shortening of the specified AV delay: suppress delivery of a biventricular pacing pulse to detect an intrinsic ventricular heart beat; determine an intrinsic PR delay using the detected intrinsic ventricular heart beat; compare the intrinsic PR delay to the specified AV delay; and when the intrinsic PR delay is longer than the specified AV delay, use information about the intrinsic PR delay to determine a lengthening of the specified AV delay.

In Example 6, the subject matter of any one of Examples 1-5 can optionally include the processor circuit configured to: store information about an intrinsic PR delay according to its ventricular heart rate or heart rate interval; and use stored information about the intrinsic PR delay data to lengthen the specified AV delay.

In Example 7, the subject matter of any one of Examples 1-6 can optionally include the processor circuit configured to provide information about at least one of AV delay, ventricular heart rate or heart rate interval, intrinsic ventricular heart rhythm, or biventricular pacing pulses to a user or process.

Example 8 can include, or can optionally be combined with any one of Examples 1-7 to include subject matter that can include scheduling delivery to a heart of a biventricular pacing pulse to be delivered in response to expiration of a specified atrioventricular (AV) delay; upon detecting an intrinsic ventricular heart beat during the specified AV delay, shortening the specified AV delay used to deliver subsequent biventricular pacing pulses to promote biventricular pacing over an underlying intrinsic ventricular heart rhythm; and shortening the specified AV delay used to deliver subsequent biventricular pacing pulses by adjusting, or adjusting to, a non-linear mapping between AV delay and ventricular heart rate interval for scheduling delivery of a biventricular pacing pulse on a next cardiac cycle following the detected intrinsic ventricular heart beat during the specified AV delay.

In Example 9, the subject matter of any one of Examples 1-8 can optionally include the non-linear mapping including a piecewise linear mapping between AV delay and ventricular heart rate interval, wherein shortening the specified AV delay includes adjusting the piecewise linear mapping.

In Example 10, the subject matter of any one of Examples 1-9 can optionally include shortening the specified AV delay including: measuring a time difference between the intrinsic ventricular heart beat detected during the specified AV delay and the scheduled delivery of a biventricular pacing pulse;

and subtracting from the specified AV delay an amount based on the time difference to obtain a shortened specified AV delay.

In Example 11, the subject matter of any one of Examples 1-10 can optionally include shortening the specified AV delay including: measuring a time difference between an atrial event and the intrinsic ventricular heart beat detected during the specified AV delay, wherein the atrial event and the intrinsic ventricular heart beat occur in the same cardiac cycle; dividing the time difference by the specified AV delay to obtain a quotient value; and multiplying the specified AV delay by the quotient value to obtain a shortened specified AV delay.

In Example 12, the subject matter of any one of Examples 1-11 can optionally include, after a specified period of time following the shortening of the specified AV delay: suppressing delivery of a biventricular pacing pulse to detect an intrinsic ventricular heart beat; determining an intrinsic PR delay using the detected intrinsic ventricular heart beat; comparing the intrinsic PR delay to the specified AV delay; and when the intrinsic PR delay is longer than the specified AV delay, using information about the intrinsic PR delay to determine a lengthening of the specified AV delay.

In Example 13, the subject matter of any one of Examples 1-12 can optionally include storing information about an intrinsic PR delay according to its ventricular heart rate or heart rate interval; and using stored information about the intrinsic PR delay data to lengthen the specified AV delay.

In Example 14, the subject matter of any one of Examples 1-13 can optionally include providing information about at least one of AV delay, ventricular heart rate or heart rate interval, intrinsic ventricular heart rhythm, or biventricular pacing pulses to a user or automated process.

The above examples can be combined with each other in various permutations or combinations. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that an apparatus and method for providing non-linear dynamic AV delay can be used, such as to help maintain cardiac resynchronization therapy (such as biventricular pacing) in patients with congestive heart failure. In such patients, 100% biventricular pacing can be useful, such as to maintain cardiac synchrony and improve hemodynamic function of the heart. However, maintaining 100% biventricular pacing over the entire ventricular pacing range can be challenging, such as due to changes over time in the heart's conduction system, such as can be caused by remodeling or changes in medication, diet, or activity, for example. In an example, a non-linear dynamic AV delay can be used to provide heart failure patients with as close to 100% biventricular pacing as possible, such as over the entire range of ventricular pacing rates.

Figure 1:
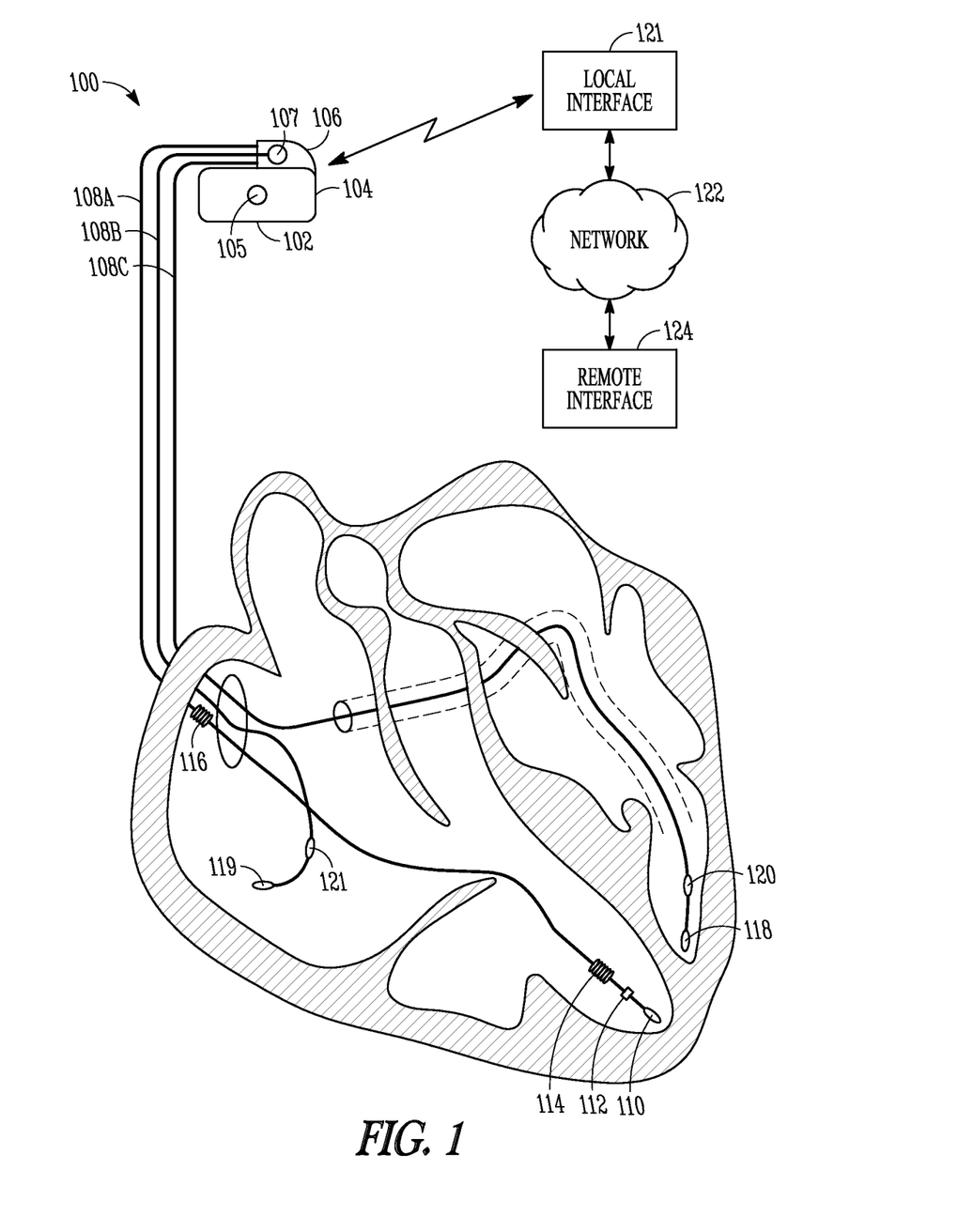
FIG. 1 shows an example of an implantable or other ambulatory cardiac rhythm management (CRM) device.

FIG. 1 shows an example of an implantable or other ambulatory cardiac rhythm management (CRM) device 100. In an example, the CRM device 100 can include an electronics unit 102 that can include a hermetically-sealed biocompatible housing 104 and a header 106 extending therefrom. The housing 104 can carry a power source and electronics. The header 106 can include one or more receptacles, such as for receiving the proximal ends of one or more intravascular leads 108A-C. In an example, the lead 108A can be an intravascular RV lead that can extend from the superior vena cava (SVC) into the right atrium (RA), and then into the right ventricle (RV). The lead 108A can include an RV apical tip electrode 110, a slightly more proximal RV ring electrode 112, a still slightly more proximal RV shock coil electrode 114, and an even more proximal RA or SVC shock coil electrode 116. The various electrodes can be used in various combinations with each other or with one or more other electrodes, such as for delivering electrical energy or sensing one or more intrinsic electrical heart signals. An intravascular CS/LV lead 108C can extend from the SVC into the RA, such as through a coronary sinus (CS) into the coronary vasculature, such as near a portion of a left ventricle (LV). In an example, this second CS/LV lead 108B can include at least a distal electrode 118 and a proximal electrode 120, from which electrostimulation energies can be delivered or intrinsic electrical heart signals can be sensed, such as in combination with each other or in combination with one or more other electrodes. An intravascular right atrial (RA) lead 108B can extend from the SVC into the RA, and can include a distal electrode 119 and a proximal electrode 121. One or more other electrodes (e.g., a housing electrode 105 on the housing 104, a header electrode 107 on the header 106, an epicardial electrode, a subcutaneous electrode located away from the heart, or an electrode located elsewhere) or leads can be used.

In an example, an implantable CRM device 100 can include a communication circuit, such as to wireless communicate unidirectionally or bidirectionally with an external local interface 121, such as a CRM device programmer, repeater, handheld device, or the like. The local interface 121 can be configured to communicate such as via a wired or wireless computer or communication network 122 to a remote interface 124, such as a remote computer or server or the like.

Figure 2:
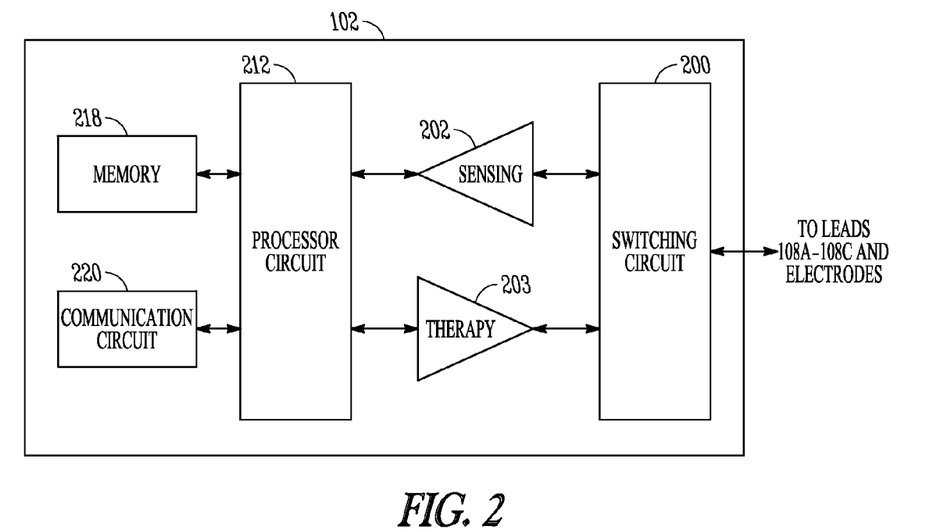
FIG. 2 shows an example of portions of the CRM device electronics unit.

FIG. 2 shows an example of portions of the CRM device electronics unit 102. In an example, this can include a switching circuit 200, such as for selectively connecting to the various electrodes such as on the leads 108A-C or elsewhere. A sensing circuit 202 can be selectively coupled to various electrodes, such as by the switching circuit 200, and can include one or more sense amplifiers, filter circuits, or other circuits such as for sensing or signal-processing one or more intrinsic electrical signals, such as intrinsic heart signals. A therapy circuit 203 can be selectively coupled to various electrodes, such as by the switching circuit 200, and can include therapy energy generation circuitry (e.g., capacitive, inductive, or other) such as for generating, storing, or delivering an electrostimulation, cardioversion, defibrillation, or other energy. In an example, the sensing circuit 202 and the therapy circuit 203 can be coupled to a processor circuit 212. In an example, the processor 212 can perform instructions, such as for signal processing of signals derived by the sensing circuit 202, or for controlling operation of the therapy circuit 203, or other operations of the CRM device 100. The processor 212 can be coupled to or include a memory circuit 218, such as for storing or retrieving instructions or data, or a communication circuit 220, such as for communicating with another location, such as with the local interface 121.

Figure 3A:
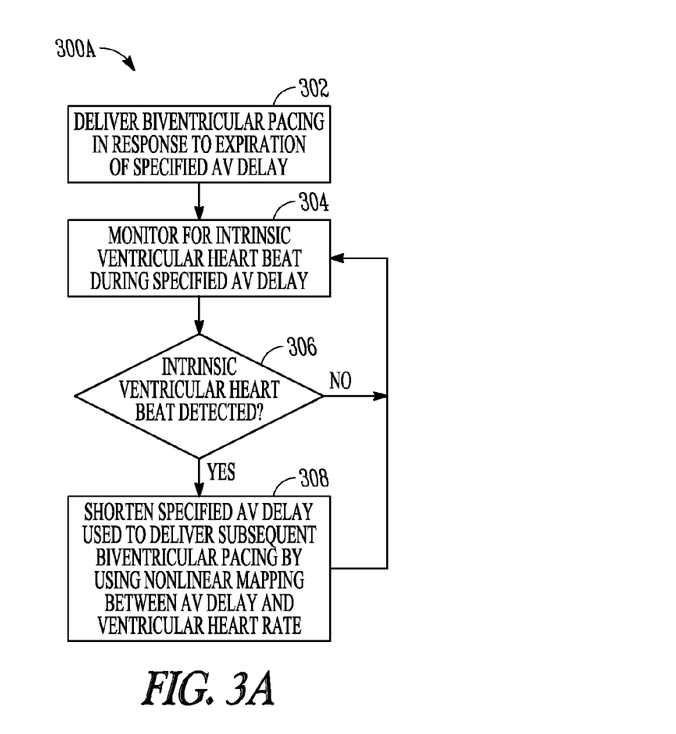
FIG. 3A shows an example of a method for using non-linear AV delay in order to maintain CRT.

FIG. 3A shows an example of a method 300A for using non-linear specified AV delay in order to maintain CRT. At 302, biventricular pacing can be delivered in response to a specified AV delay (e.g., a programmed AV delay). In an example, the specified AV delay can be specified as an initial fixed AV delay or an initial dynamic (e.g., rate-dependent) AV delay. In an example, the specified AV Delay can be set by the physician, such as through an echocardiography-based optimization technique or through a CRM device 100 or system-based optimization technique, such as described by way of example in Ding et al. U.S. Pat. No. 6,144,880 entitled "CARDIAC PACING USING ADJUSTABLE ATRIO-VENTRICULAR DELAYS," assigned to the assignee of the present application, the disclosure of which is incorporated herein by reference in its entirety. At 304, the patient's cardiac function can be monitored, such as to detect an intrinsic ventricular heart beat occurring during the specified AV delay (e.g., before the expiration of the specified AV delay). Such an intrinsic ventricular heart beat can be referred to as a "breakthrough" intrinsic ventricular beat because it indicates that the patient's intrinsic ventricular heart rate is superseding the paced heart rate. This can occur, for example, when the paced heart rate is too slow to meet the patient's cardiac demand, such as during exercise. When the paced heart rate is too slow, the specified AV delay can be too long (e.g., because of a physiological response in which intrinsic AV delay shortens as ventricular heart rate increases, and lengthens as the ventricular heart rate decreases). Furthermore, breakthrough intrinsic ventricular beats can be indicative of a specified AV delay that is too long (and a paced heart rate that is too slow) due to changes in the patient's cardiac conduction system caused by remodeling, changes in medication, or changes in diet, for example.

In an example, breakthrough intrinsic ventricular heart beats can include a breakthrough intrinsic right ventricular heart beat or a breakthrough intrinsic left ventricular heart beat. Either one or both of the breakthrough intrinsic right and left ventricular beats can be indicative of a specified AV delay that is too long. A breakthrough intrinsic right ventricular beat alone, or a breakthrough intrinsic left ventricular beat alone, can be indicative of either a specified AV delay that is too long or a specified interval between ventricular paces (specified VV interval) that is too long.

Figure 4A:
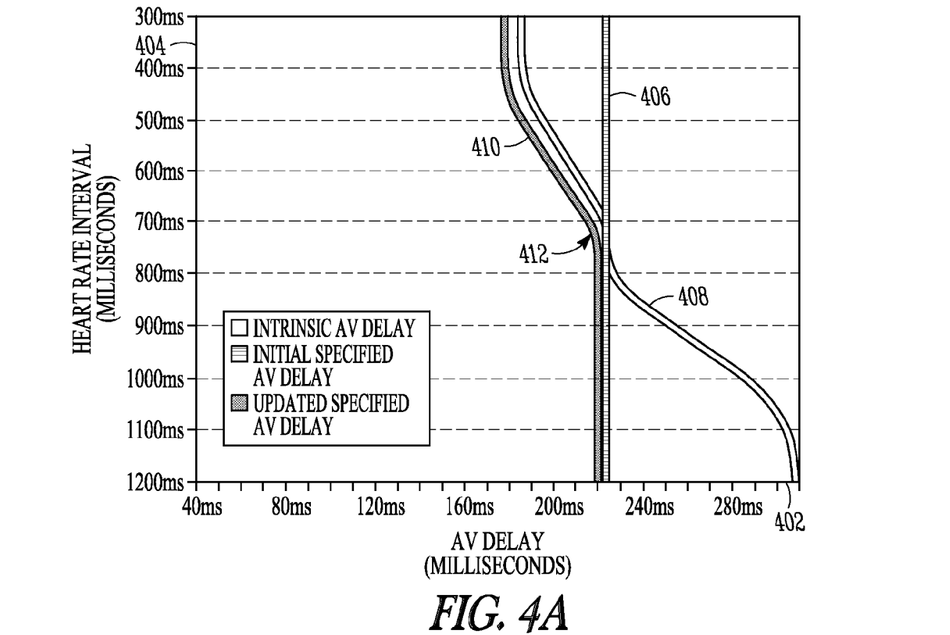
FIG. 4A shows an example of a plot of AV delay interval versus ventricular heart rate interval.

FIG. 4A is an example of a plot of specified AV delay interval versus ventricular heart rate interval in which an example of a breakthrough intrinsic ventricular heart beat is shown. The x-axis 402 represents AV delay measured in milliseconds (ms). The y-axis 404 represents ventricular heart rate interval measured in milliseconds. Line 406 represents the initial specified AV delay, which can be automatically or manually programmed into CRM device 100. In this example, the specified AV delay is about 220 ms. Line 408 represents the patient's intrinsic AV delay at various ventricular heart rates. Line 410 represents an updated, or shortened, specified AV delay at various ventricular heart rates or heart rate intervals. As shown, the updated specified AV delay line 410 is the same as the initial specified AV delay line 406 until the intrinsic AV delay line 408 crosses the initial specified AV delay line 406, indicating a breakthrough intrinsic ventricular heart beat, at arrow 412. At this point, the updated specified AV delay line 410 can be adjusted, either automatically by CRM device 100 or manually by a user, such that the patient's specified AV delay is shortened, in this example, beginning at a ventricular heart rate of 86 bpm (the ventricular heart rate at which the intrinsic ventricular beat was detected), which corresponds to a ventricular heart rate interval of 700 ms, and continuing at higher ventricular heart rates (or shorter ventricular heart rate intervals). In this example, at ventricular heart rates of 86 bpm or higher (or ventricular heart rate interval of 700 ms or shorter), the updated specified AV delay line 410 approximately follows the intrinsic AV delay line 408, thereby mimicking the patient's physiological PR interval as a function of heart rate, which is believed can correspond to a beneficial or optimum AV delay at which cardiac demand can be efficiently met.

Returning now to FIG. 3A, at 306 it can be determined whether a breakthrough intrinsic ventricular heart beat is detected during a then-current specified AV delay. If no breakthrough intrinsic beat is detected, the process can flow back to 304, where monitoring for breakthrough intrinsic beats can continue. If, at 306, a breakthrough intrinsic ventricular heart beat is detected, then, at 308, the specified AV delay used to deliver later biventricular pacing can be shortened, either automatically by the CRM device 100 or manually by a user, such as by using a non-linear mapping between the specified AV delay and the ventricular heart rate interval, such as with a non-linearity occurring at the heart rate interval at which the breakthrough intrinsic ventricular beat was detected. Shortening of the specified AV delay can allow for CRT to be maintained (and can help avoid further breakthrough intrinsic ventricular beats) at higher ventricular rates. The specified AV delay can be shortened by adjusting (e.g., in the case of an initial non-linear dynamic specified AV delay), or adjusting to (e.g., in the case of an initial linear dynamic or fixed specified AV delay), a non-linear mapping between specified AV delay and ventricular heart rate intervals, such as with a deviation away from linearity occurring at ventricular heart rates that are equal to or greater than the ventricular heart rate at which the breakthrough intrinsic ventricular beat was detected. The shortened specified AV delay can be used to schedule delivery of subsequent biventricular pacing pulses, such as beginning with the next cardiac cycle following the detected breakthrough intrinsic ventricular heart beat. Once the specified AV delay has been shortened at 308 in response to a detected breakthrough intrinsic ventricular heart beat, the process can flow back to 304, where monitoring for additional breakthrough intrinsic beats can continue.

In an example, the non-linear mapping between specified AV delay and ventricular heart rate can include a piecewise linear mapping between specified AV delay and ventricular heart rate interval, and the shortening of the specified AV delay can include adjusting the piecewise linear mapping. For example, the specified AV delay can be adjusted in multiple "segments," where each segment adjustment occurs at a linearity breakpoint at a ventricular heart rate interval at which a breakthrough intrinsic ventricular beat was detected. This can result in a piecewise linear non-linear dynamic AV delay that includes multiple fixed or dynamic specified AV delay segments.

Figure 4B:
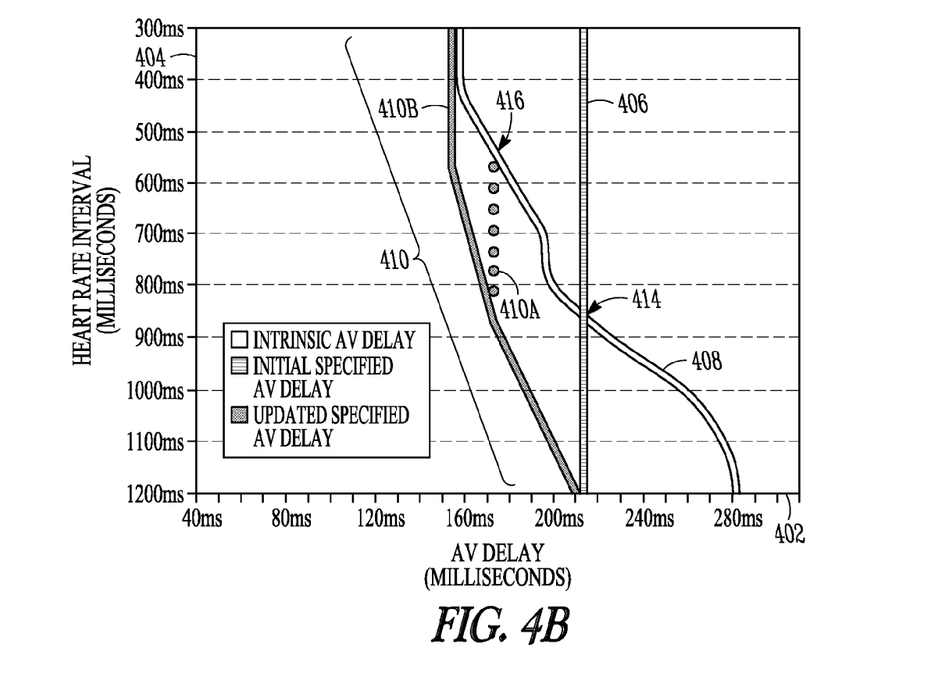
FIG. 4B shows an example of a piecewise non-linear dynamic AV delay interval vs. ventricular heart rate interval.

FIG. 4B shows an example of a piecewise-linear non-linear dynamic AV delay interval (vs. ventricular heart rate interval)

that can include multiple specified AV delay segments. At arrow 414, intrinsic AV delay line 408 crosses the specified AV delay line 406 at a ventricular heart rate of about 71 bpm (or ventricular heart rate interval of about 850 ms), indicating a breakthrough ventricular heart beat at that ventricular heart rate. At this heart rate, the patient's specified AV delay can be updated, either automatically by the CRM device 100 or manually by a user, such as by creating a shortened fixed specified AV delay, which is represented in this example by line segment 410A, beginning at a ventricular heart rate of 71 bpm (e.g., the ventricular heart rate at which the intrinsic ventricular beat was detected) and continuing at higher ventricular heart rates (or shorter heart rate intervals). The updated specified AV delay represented by line 410A can be thought of as a first "segment" adjustment of AV delay. At arrow 416, the intrinsic AV delay line 408 crosses the updated specified AV delay line segment 410A at a ventricular heart rate of about 109 bpm (or a ventricular heart rate interval of about 550 ms), indicating a second breakthrough ventricular heart beat at such higher heart rate. In response to the second breakthrough ventricular heart beat, the patient's specified AV delay can be updated again, either automatically by the CRM device 100 or manually by a user, such as by creating a second shortened specified AV delay, represented here by line segment 410B. The updated specified AV delay represented by line 410B can be thought of as a second "segment" adjustment of AV delay. Further segment adjustments can be made in response to other breakthrough ventricular heart beats. Thus, by piecing together the segment adjustments, a piecewise-linear non-linear dynamic AV specified delay, represented by line 410, can be generated and extrapolated along the entire desired ventricular pacing range.

In an example, shortening the specified AV delay using a piecewise-linear non-linear dynamic specified AV delay can include shortening the specified AV delay by a time difference or by a specified percentage. For example, shortening can include subtracting, from the specified AV delay, the time difference (e.g., measured in milliseconds) between the occurrence of a breakthrough intrinsic ventricular heart beat and the scheduled delivery of a biventricular pacing pulse. In an example, shortening the specified AV delay can include measuring a time difference between a detected atrial event and an intrinsic ventricular heart beat detected during the specified AV delay (and during the same cardiac cycle as the detected atrial event), which can be representative of the patient's intrinsic PR interval (also referred to as intrinsic AV delay). The duration of the specified AV delay can then be compared to the time period representing the intrinsic PR interval, and the time period representing the intrinsic PR interval can be expressed as a specified percentage of the specified AV delay (e.g., intrinsic PR interval is 85% of specified AV delay). The specified AV delay can then be shortened by the specified percentage (e.g., multiply the then-current specified AV delay by 85% to obtain a new shortened specified AV delay).

Figure 3B:
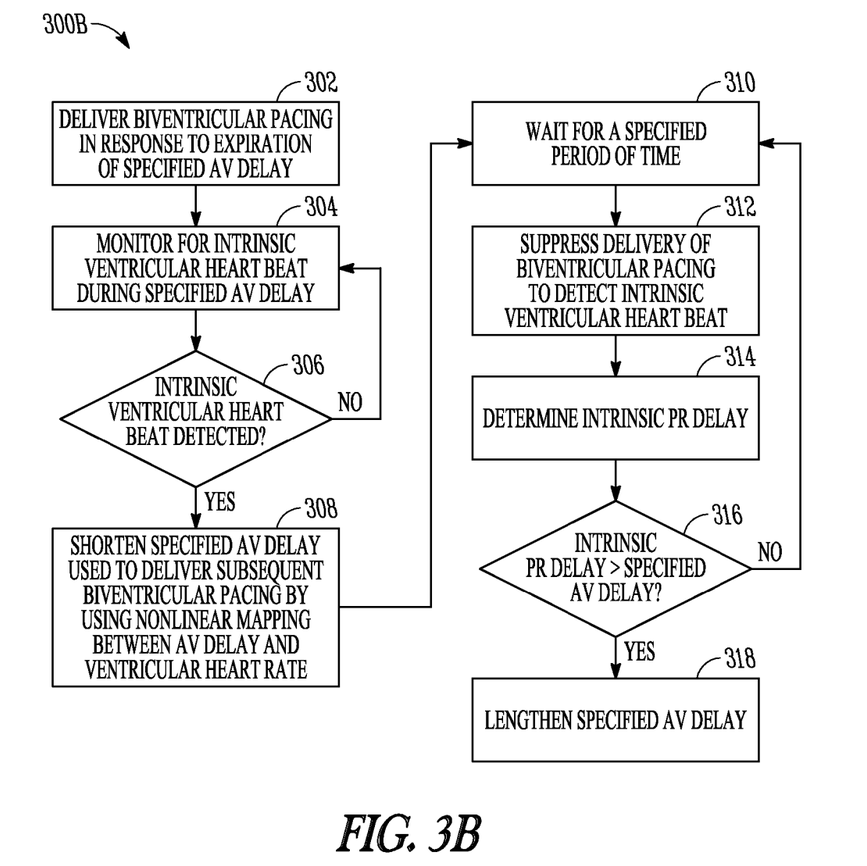
FIG. 3B shows an example of a method for using non-linear AV delay in order to maintain CRT.

FIG. 3B shows an example of a method 300B for using non-linear AV delay, such as in order to maintain CRT. Steps 302-308 can be the same as those described above with respect to FIG. 3A. The method 300B can continue after, at 310, a specified period of time has elapsed following shortening of the specified AV delay. At 312, delivery of biventricular pacing can be temporarily suppressed, such as in order to detect an underlying intrinsic ventricular heart beat. Once an intrinsic ventricular heart beat has been detected, an intrinsic PR delay can be determined at 314 such as by using information about the detected ventricular heart beat. The intrinsic PR interval can be determined by measuring the time difference between an atrial event and a detected intrinsic ventricular heart beat within the same cardiac cycle. In an example, multiple intrinsic ventricular beats can be detected at 312 before the intrinsic PR delay is determined at 314. Information about multiple intrinsic ventricular beats can be collected, stored, and used to determine the intrinsic PR delay. For example, a central tendency measurement of the time differences between multiple atrial events and multiple intrinsic ventricular beats, each atrial event and intrinsic beat being within the same cardiac cycle, can be used to determine the intrinsic PR delay. In addition, information about multiple determinations of intrinsic PR delay can be stored, such as according to the intrinsic ventricular heart rate used to determine the intrinsic PR delay, and the stored information about the intrinsic PR delays can be used to lengthen the specified AV delay. For example, a central tendency measurement of the stored intrinsic PR delay determinations can be used to lengthen the specified AV delay.

At 316, the intrinsic PR interval can be compared to the specified AV delay. If the intrinsic PR delay is shorter than or equal to the specified AV delay, the process can revert to 310. However, if the intrinsic PR delay is longer than the specified AV delay, then, at 316, information about the intrinsic PR delay can be used to determine a lengthening of the specified AV delay. Lengthening of the specified AV delay can be desirable when the intrinsic PR delay is longer than the specified AV delay, such as in order to maintain cardiac synchrony and improve hemodynamic function of the heart. The lengthening of the specified AV delay can include using a time difference or a specified percentage. For example, if the intrinsic PR delay is 20 ms longer than the specified AV delay, then the specified AV delay can be lengthened by 20 ms (or by some specified small increment less, to promote CRT). In an example, if the intrinsic PR delay is 20% longer than the specified AV delay, the specified AV delay can be lengthened by 20% (or by some smaller specified percentage, such as to promote CRT), for example. Thus, the AV delay interval can be dynamically shortened, such as in response to breakthrough ventricular beats, as described above, and dynamically lengthened, such as by occasionally looking for the underlying intrinsic PR delay, and lengthening the AV delay to be close to the intrinsic PR delay interval, but slightly shorter, so as to still promote CRT electrostimulations.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. Although the examples described herein apply to a non-linear AV delay, the invention can further be applied to a non-linear VV delay. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
   a cardiac rhythm management device comprising:
      an atrial sensing circuit, configured to sense an atrial event;
      a ventricular pacing circuit configured to deliver biventricular pacing pulses;
      a ventricular sensing circuit configured to detect an intrinsic ventricular heart beat;
      a memory comprising instructions; and
      a processor, coupled to the atrial sensing circuit, the ventricular pacing circuit, the ventricular sensing circuit, and the memory, wherein the instructions, when executed by the processor, cause the processor to:
         obtain an initial specified atrioventricular (AV) delay;
         detecting an expiration of the initial specified AV delay;
         schedule delivery to a heart of a first biventricular pacing pulse to be delivered in response to expiration of the initial specified AV delay;
         upon detecting an intrinsic ventricular heart beat during the initial specified AV delay, calculate an intrinsic ventricular heart rate interval and obtain a shortened specified AV delay used to deliver subsequent biventricular pacing by adjusting, or adjusting to, a specified non-linear mapping between the initial specified AV delay and the intrinsic ventricular heart rate interval; and
         detect the expiration of the shortened specified AV delay and schedule delivery of a second biventricular pacing pulse on a next cardiac cycle following the detected intrinsic ventricular heart beat in response to expiration of the shortened specified AV delay;
         calculate at least one of:
            a time difference between the intrinsic ventricular heart beat detected during the initial specified AV delay and the scheduled delivery of the first biventricular pacing pulse; and
            a time difference between an atrial event and the intrinsic ventricular heart beat detected during the initial specified AV delay;
         wherein the shortened specified AV delay is determined based on at least one of:
            the time difference between the intrinsic ventricular heart beat detected during the initial specified AV delay and the scheduled delivery of the first biventricular pacing pulse; and
            the time difference between an atrial event and the intrinsic ventricular heart beat detected during the initial specified AV delay.

2. The apparatus of claim 1, wherein the processor circuit is configured to adjust, or adjust to, the specified non-linear mapping using a piecewise linear mapping between the initial specified AV delay and the intrinsic ventricular heart rate interval.

3. The apparatus of claim 1, wherein the processor circuit is configured to:
   subtract from the initial specified AV delay an amount based on the calculated time difference to determine the shortened specified AV delay.

4. The apparatus of claim 1, wherein the processor circuit is configured to:
   divide the calculated time difference by the initial specified AV delay to obtain a quotient value; and
   multiply the initial specified AV delay by the quotient value to determine the shortened specified AV delay.

5. The apparatus of claim 1, wherein the processor circuit is configured to, after a specified period of time following delivery of the second biventricular pacing pulse:
   suppress delivery of a biventricular pacing pulse to detect an intrinsic ventricular heart beat;
   determine an intrinsic PR delay using the detected intrinsic ventricular heart beat;
   compare the intrinsic PR delay to the shortened specified AV delay; and
   when the intrinsic PR delay is longer than the shortened specified AV delay, use information about the intrinsic PR delay to determine a lengthened specified AV delay.

6. The apparatus of claim 5, wherein the processor circuit is configured to:
   store information about an intrinsic PR delay according to its ventricular heart rate or heart rate interval; and
   use stored information about the intrinsic PR delay data to determine the lengthened specified AV delay.

7. The apparatus of claim 1, wherein the processor circuit is configured to provide information about at least one of the initial or shortened AV delay, intrinsic ventricular heart rate, the intrinsic ventricular heart rate interval, intrinsic ventricular heart rhythm, or biventricular pacing pulses to a user or automated process.

8. A method comprising:
   obtaining an initial specified atrioventricular (AV) delay;

detecting an expiration of the initial specified AV delay;
scheduling delivery to a heart of a first biventricular pacing pulse to be delivered in response to expiration of the initial specified AV delay;
upon detecting an intrinsic ventricular heart beat during the initial specified AV delay, calculating an intrinsic ventricular heart rate interval, obtaining a shortened specified AV delay used to deliver subsequent biventricular pacing by adjusting, or adjusting to, a specified non-linear mapping between the initial specified AV delay and an intrinsic ventricular heart rate interval; and
detecting the expiration of the shortened specified AV delay and scheduling delivery of a second biventricular pacing pulse on a next cardiac cycle following the detected intrinsic ventricular heart beat in response to expiration of the shortened specified AV delay; and
calculating at least one of:
  a time difference between the intrinsic ventricular heart beat detected during the initial specified AV delay and the scheduled delivery of the first biventricular pacing pulse; and
  a time difference between an atrial event and the intrinsic ventricular heart beat detected during the initial specified AV delay; and
wherein the shortened specified AV delay is determined based on at least one of:
  the time difference between the intrinsic ventricular heart beat detected during the initial specified AV delay and the scheduled delivery of the first biventricular pacing pulse; and
  the time difference between an atrial event and the intrinsic ventricular heart beat detected during the initial specified AV delay.

9. The method of claim 8, wherein obtaining the shortened specified AV delay used to deliver subsequent biventricular pacing by adjusting, or adjusting to, the specified non-linear mapping includes using a piecewise linear mapping between the initial specified AV delay and the intrinsic ventricular heart rate interval.

10. The method of claim 8, wherein obtaining the shortened specified AV delay includes:
subtracting from the initial specified AV delay an amount based on the calculated time difference to obtain the shortened specified AV delay.

11. The method of claim 8, wherein obtaining the shortened specified AV delay includes:
dividing the calculated time difference by the initial specified AV delay to obtain a quotient value; and
multiplying the initial specified AV delay by the quotient value to obtain the shortened specified AV delay.

12. The method of claim 8, comprising, after a specified period of time following delivery of the second biventricular pacing pulse:
suppressing delivery of a biventricular pacing pulse to detect an intrinsic ventricular heart beat;
determining an intrinsic PR delay using the detected intrinsic ventricular heart beat;
comparing the intrinsic PR delay to the shortened specified AV delay; and
when the intrinsic PR delay is longer than the shortened specified AV delay, using information about the intrinsic PR delay to determine a lengthened specified AV delay.

13. The method of claim 12, comprising:
storing information about an intrinsic PR delay according to its ventricular heart rate or heart rate interval; and
using stored information about the intrinsic PR delay data to determine the lengthened specified AV delay.

14. A non-transitory device-readable medium including instructions that, when performed by the device, comprise:
obtaining an initial specified atrioventricular (AV) delay;
detecting an expiration of the initial specified AV delay;
scheduling delivery to a heart of a first biventricular pacing pulse to be delivered in response to expiration of the initial specified AV delay;
upon detecting an intrinsic ventricular heart beat during the initial specified AV delay, calculating an intrinsic ventricular heart rate interval, obtaining a shortened specified AV delay used to deliver subsequent biventricular pacing by adjusting, or adjusting to, a specified non-linear mapping between the initial specified AV delay and the intrinsic ventricular heart rate interval; and
detecting the expiration of the shortened specified AV delay and scheduling delivery of a second biventricular pacing pulse on a next cardiac cycle following the detected intrinsic ventricular heart beat in response to expiration of the shortened specified AV delay,
calculating at least one of:
  a time difference between the intrinsic ventricular heart beat detected during the initial specified AV delay and the scheduled delivery of the first biventricular pacing pulse; and
  a time difference between an atrial event and the intrinsic ventricular heart beat detected during the initial specified AV delay; and
wherein the shortened specified AV delay is determined based on at least one of:
  the time difference between the intrinsic ventricular heart beat detected during the initial specified AV delay and the scheduled delivery of the first biventricular pacing pulse; and
  the time difference between an atrial event and the intrinsic ventricular heart beat detected during the initial specified AV delay.

15. The device-readable medium of claim 14, wherein obtaining the shortened specified AV delay used to deliver subsequent biventricular pacing by adjusting, or adjusting to, the specified non-linear mapping includes using a piecewise linear mapping between the initial specified AV delay and the intrinsic ventricular heart rate interval.

16. The device-readable medium of claim 14, wherein obtaining the shortened specified AV delay includes:
subtracting from the initial specified AV delay an amount based on the calculated time difference to obtain the shortened specified AV delay.

17. The device-readable medium of claim 14, wherein obtaining the shortened specified AV delay includes:
dividing the calculated time difference by the initial specified AV delay to obtain a quotient value; and
multiplying the initial specified AV delay by the quotient value to obtain the shortened specified AV delay.

18. The device-readable medium of claim 14, comprising, after a specified period of time following delivery of the second biventricular pacing pulse:
suppressing delivery of a biventricular pacing pulse to detect an intrinsic ventricular heart beat;
determining an intrinsic PR delay using the detected intrinsic ventricular heart beat;
comparing the intrinsic PR delay to the shortened specified AV delay; and
when the intrinsic PR delay is longer than the shortened specified AV delay, using information about the intrinsic PR delay to determine a lengthened specified AV delay.

19. The device-readable medium of claim 18, comprising: comprising:

storing information about an intrinsic PR delay according to its ventricular heart rate or heart rate interval; and using stored information about the intrinsic PR delay data to determine the lengthened specified AV delay.

20. The device-readable medium of claim 14, comprising:

providing information about at least one of the initial or shortened AV delay, intrinsic ventricular heart rate, the intrinsic ventricular heart rate interval, intrinsic ventricular heart rhythm, or biventricular pacing pulses to a user or automated process.

* * * * *